(12) United States Patent
Matarazzo

(10) Patent No.: US 12,390,217 B2
(45) Date of Patent: Aug. 19, 2025

(54) BICEP TENODESIS ARTHROSCOPIC STAPLE

(71) Applicant: Marc F Matarazzo, Longview, TX (US)

(72) Inventor: Marc F Matarazzo, Longview, TX (US)

( * ) Notice: Subject to any disclaimer, the term of this patent is extended or adjusted under 35 U.S.C. 154(b) by 268 days.

(21) Appl. No.: 17/942,905

(22) Filed: Sep. 12, 2022

(65) Prior Publication Data
US 2024/0081815 A1 Mar. 14, 2024

(51) Int. Cl.
| | | |
|---|---|---|
| A61B 17/064 | (2006.01) | |
| A61B 17/04 | (2006.01) | |
| A61B 17/068 | (2006.01) | |
| A61B 17/08 | (2006.01) | |

(Continued)

(52) U.S. Cl.
CPC .......... *A61B 17/0642* (2013.01); *A61B 17/10* (2013.01); *A61B 17/0401* (2013.01); *A61B 2017/0414* (2013.01); *A61B 2017/0427* (2013.01); *A61B 2017/0446* (2013.01); *A61B 2017/0464* (2013.01); *A61B 17/064* (2013.01); *A61B 2017/0641* (2013.01); *A61B 17/0644* (2013.01); *A61B 2017/0646* (2013.01); *A61B 17/068* (2013.01); *A61B 17/0682* (2013.01); *A61B 17/08* (2013.01); *A61B 2017/081* (2013.01); *A61B 17/1604* (2013.01)

(58) Field of Classification Search
CPC ............ A61B 17/0642; A61B 17/0401; A61B 17/0682; A61B 17/10; A61B 17/1604; A61B 17/4684; A61B 17/064; A61B 17/0644; A61B 17/068; A61B 17/08; A61B 17/083; A61B 2017/0427; A61B 2017/0414; A61B 2017/0641; A61B 2017/0645; A61B 2017/0646; A61B 2017/081; A61B 2017/0464; A61B 2017/0445; A61B 2017/0403; A61B 2017/0404; A61B 2017/0406; A61B 2017/0446
USPC ... 606/75, 53, 280, 283–285, 300, 329, 330, 606/78, 86 R, 87, 96, 104, 916, 232
See application file for complete search history.

(56) References Cited

U.S. PATENT DOCUMENTS

| | | | | |
|---|---|---|---|---|
| 4,988,351 A | * | 1/1991 | Paulos .................. | A61F 2/0811 623/13.12 |
| 6,280,472 B1 | * | 8/2001 | Boucher ............ | A61B 17/0642 623/13.11 |

(Continued)

*Primary Examiner* — Marcela I. Shirsat
(74) *Attorney, Agent, or Firm* — The Rapacke Law Group, P.A.; Andrew Rapacke

(57) ABSTRACT

An arthroscopic staple used by a surgeon to arthroscopically fixate the tendon of the long head of the biceps brachii in-situ to the humerus within the bicipital groove when performing an arthroscopic high supra-pectoral biceps tenodesis is provided. The arthroscopic staple includes a cylindrical body, and the top of the cylindrical body includes a center aperture formed by a central vertical cavity located at the center of the cylindrical body. The cylindrical body includes a first aperture and a second aperture formed by a first vertical cavity and a second vertical cavity radially displaced from the center of the cylindrical body and a pair of protrusions located on the underside of the cylindrical body. Each of the protrusions includes a sharp point and at least one barb.

18 Claims, 9 Drawing Sheets

(51) Int. Cl.
*A61B 17/10* (2006.01)
*A61B 17/16* (2006.01)

(56) References Cited

U.S. PATENT DOCUMENTS

| | | | |
|---|---|---|---|
| 2002/0065536 A1* | 5/2002 | Hart | A61B 17/0487 606/232 |
| 2009/0030434 A1* | 1/2009 | Paz | A61B 17/064 606/1 |
| 2009/0234386 A1* | 9/2009 | Dean | A61B 17/0401 606/232 |
| 2016/0242771 A1* | 8/2016 | Weinstein | A61B 17/842 |

* cited by examiner

BICEP TENODESIS ARTHROSCOPIC STAPLE

FIELD

The present disclosure relates to an arthroscopic staple configured to secure a tendon of the long head of the biceps to a humerus during a surgical procedure, specifically the apparatus is an arthroscopic staple to be used in a biceps tenodesis procedure which involves cutting the tendon of the long head of the biceps off the labrum or the pad of cartilage inside the glenoid (socket portion of the shoulder joint) and reattaching the tendon of the long head to the humerus or the bone of the upper arm, or to various other local soft tissues.

BACKGROUND OF THE INVENTION

The tendon of the long head of the biceps has long been recognized as a source of pain in the shoulder. There are a number of surgical treatment options to address this including the disclosed biceps tenodesis procedure and a biceps tenotomy procedure. In contrast to the biceps tenodesis procedure where the tendon of the long head of the biceps is reattached to the humerus, or local soft tissue, in the biceps tenotomy procedure the tendon of the long head is cut at its base by the top of the shoulder socket and allowed to retract out of the joint and heal to the humerus or surrounding local soft tissue over a few weeks. Generally, the biceps tenodesis procedure is preferred over the biceps tenotomy procedure because it maintains elbow flexion and strength, avoids muscle cramping, and preserves the physical appearance of the shoulder area. Candidates for the biceps tenodesis procedure include patients with long head biceps tears involving more than 50% of the tendon, patients with a medial long head of the biceps subluxation/dislocation combined with a subscapularis tear, and some superior labral (SLAPS) tears.

Conventional devices for reattaching the tendon of the long head of the biceps to the humerus or the bone of the upper arm include suture anchors, bone anchors, bone tunnels, interference screws, cortical buttons, soft tissue fixation, spears with rivets such as the ZIMMER SNAP-SHOT™, and bolts such as the ZIMMER™. However, none of these conventional devices have all of the advantages of the proposed arthroscopic staple and the biceps tenodesis procedure that it enables. For example, in the case of suture anchors the tendon of the long head must be moved, multiple sutures must be tied off, complicated knot tying is required, and the tendon must heal to the surface of cortical bone. Bone tunnels require a larger incision, the tendon of the long head must be manipulated and prepared outside of the joint, and multiple tunnels must be drilled. Bone tunnels further require sutures to be passed through tunnels and knots tied. Lastly, it is difficult to assess the biceps tension when using bone tunnels. Interference screws and bolts like the ZIMMER™ bolt, require the tendon of the long head to be manipulated and prepared outside of the joint. Interference screws further require the passing of multiple sutures. Lastly, it is difficult to assess the biceps tension when using an interference screw. Soft tissue fixation and spear tissue fixation both require a large incision and multiple sutures to be passed and tied. Lastly a spear with rivets, for example the ZIMMER SNAPSHOT™, require the tendon of the long head to be manipulated and impaled, potentially weakening the tendon of the long head. Additionally, this device does not allow for back-up fixation.

What is needed is an apparatus that allows the biceps tenodesis procedure to be performed with the tendon of the long head in its in-situ position while still intact so that the tension of the tendon of the long head can be maintained.

The disclosed arthroscopic staple allows the biceps tenodesis procedure to be performed expediently through a standard arthroscopic portal incision with the tendon of the long head in its in-situ position at the inferior portion of the bicipital groove with the tendon of the long head still attached proximally, thereby maintaining the tendon of the long head in-situ length, and therefore in-situ tension, with the aid of an arthroscopic camera. Further, unlike a conventional spear with rivets, the disclosed arthroscopic staple allows for a secondary fixation option using a suture(s) in addition to the primary arthroscopic staple anchor fixation and does not require penetration through the tendon, which may weaken the tendon and compromise the fixation.

SUMMARY OF THE INVENTION

The present disclosure relates to an arthroscopic staple configured to secure a tendon of the long head of the biceps to a humerus during a surgical procedure, specifically the apparatus is an arthroscopic staple to be used in a biceps tenodesis procedure which involves cutting the tendon of the long head off the labrum or the pad of cartilage inside the glenoid (socket portion of the shoulder joint) and reattaching the tendon of the long head to the humerus or the bone of the upper arm.

Additional features and advantages of the embodiments disclosed herein will be set forth in the detailed description that follows, and in part will be clear to those skilled in the art from that description or recognized by practicing the embodiments described herein, including the detailed description which follows, the claims, as well as the appended drawings.

In various embodiments, an arthroscopic staple used by a surgeon to arthroscopically fixate the long head biceps tendon in-situ to the bone in the biceps groove when performing an arthroscopic high supra-pectoral biceps tenodesis includes a cylindrical body. The top of the cylindrical body includes a center aperture formed by a central vertical cavity located at the center of the cylindrical body. The cylindrical body includes a first aperture and a second aperture formed by a first vertical cavity and a second vertical cavity radially displaced from the center of the cylindrical body and a pair of protrusions located on the underside of the cylindrical body. Each of the protrusions includes a sharp point and at least one barb.

In various embodiments, each of the at least one barb is a sharp projection located near and angled away from the end of the sharp point of each of the first pair of protrusions to make extraction of the arthroscopic staple difficult from a bone.

In various embodiments, the cylindrical body of the arthroscopic staple has a diameter that is between about 5 mm and about 10 mm. For example, the diameter of the cylindrical body is one of about 6 mm, about 7 mm, and about 8 mm.

In various embodiments, the cylindrical body of the arthroscopic staple has a height that is between about 3 mm and about 7 mm. For example, the height of the cylindrical body is about 5 mm. In some embodiments, the cylindrical body of the arthroscopic staple has a low-profile body with rounded corners.

In various embodiments, the length of each protrusion of the cylindrical body is between about 10 mm and about 20 mm. For example, the length of each protrusion is about 15 mm.

In various embodiments, the arthroscopic staple is made of a polyether ether ketone (PEEK) material.

In various embodiments, the first aperture and the second aperture of the cylindrical body are configured to allow at least one suture looped around the biceps tendon or through the biceps tendon to be fed through the cylindrical body and tied off.

In various embodiments, a portion of the underside of the cylindrical body between the first pair of protrusions is contoured to lockingly engage the biceps tendon, which has a width of about 6 mm and a thickness of about 3 mm. In some embodiments, at least the portion of the underside of the cylindrical body is coated with a material having a high coefficient of static friction.

In various embodiments, the center aperture of the cylindrical body is configured to lockingly engage the distal end of an inserter rod. For example, the distal end of the inserter rod is threaded to match a threaded recess in the center aperture of the cylindrical body. The inserter rod is configured to tap the first pair of protrusions of the cylindrical body into the bone.

In various embodiments, the center aperture of the cylindrical body and a distal end of a metal tap inserter are configured to form an interference fit. In some embodiments, the interference fit is achieved by making the internal diameter of the center aperture of the cylindrical body slightly smaller than an external diameter of the metal tap inserter. In some embodiments, the internal diameter of the center aperture of the cylindrical body is equal to or less than 3 mm. The metal tap inserter is configured to tap the first pair of protrusions of the cylindrical body into the bone.

In various embodiments, the cylindrical body further includes a second pair of protrusions located on the underside of the cylindrical body. Each of the protrusions includes a sharp point, and at least one barb with a projection located near and angled away form an end of the sharp point. The barb(s) makes extraction of the arthroscopic staple from a bone difficult.

In some embodiments, a metal tap inserter for an arthroscopic staple includes a solid cylindrical rod made of a metal material. The distal end of the solid cylindrical rod is configured to be lockingly coupled to a recess in an arthroscopic staple and the near end of the solid cylindrical rod is configured to be gently and repeatedly struck with a surgical mallet.

In various embodiments, the length of the solid cylindrical rod is between about 15 cm and about 25 cm. For example, the length of the solid cylindrical rod is 22 cm. In some embodiments, the diameter of the solid cylindrical rod is equal to or less than about 3 mm.

In various embodiments, only the tip of the distal end of the solid cylindrical rod is equal to or less than about 3 mm. The body of the cylindrical rod is between about 6.5 mm and about 8 mm in diameter. In some embodiments, the tip portion of the distal end of the solid cylindrical rod has a shoulder.

In various embodiments, the distal end of the solid cylindrical rod has a thread that lockingly couples with a threaded recess in the arthroscopic staple. In some embodiments, the tip of the distal end of the solid cylindrical rod has a taper and no thread.

In various embodiments, the material of the solid rod of the metal tap inserter is one or more of a surgical grade stainless steel, a cobalt-chromium alloy, a titanium alloys, and the like.

In some embodiments, a metal tap pitchfork for an arthroscopic staple includes a pitchfork body and a solid cylindrical rod coupled to an upper face of the pitchfork body, The pitchfork metal tap pitchfork further includes a pair of protrusions coupled to the underside of the pitchfork body.

In various embodiments, the material that the metal tap pitchfork is made of is one or more of surgical grade stainless steel, cobalt-chromium alloy, titanium alloy, and the like.

In various embodiments, each of the protrusions located on an underside of the pitchfork body has a length of about 15 mm and tapers to a sharp point. The sharp point is operable to make a pilot hole for an arthroscopic staple. The length of the solid cylindrical rod is between about 15 cm and about 25 cm, and the distance between the pair of protrusions is 6 mm.

Both the foregoing general description and the following detailed description present embodiments intended to provide an overview or framework for understanding the nature and character of the embodiments disclosed herein. The accompanying drawings are included to provide further understanding and are incorporated into and constitute a part of this specification. The drawings illustrate various embodiments of the disclosure, and together with the description explain the principles and operations thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features and advantages of the present disclosure will be more fully described in, or rendered obvious by, the following detailed description of the preferred embodiments, which are to be considered together with the accompanying drawings, wherein like numbers refer to like parts and further, wherein.

Figure 1:
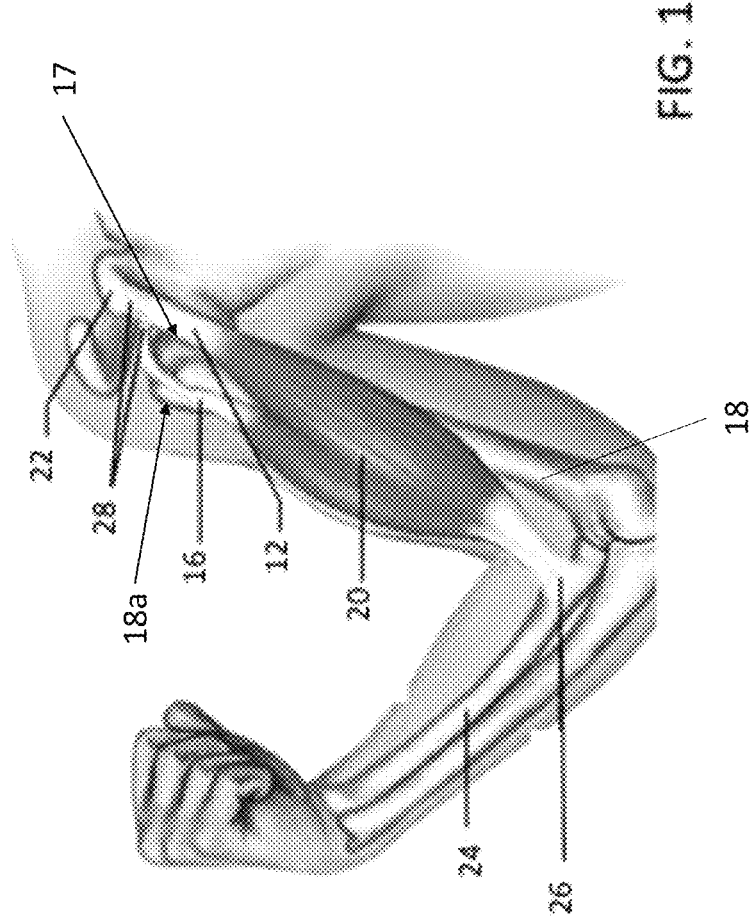
FIG. 1 is a front left perspective view of the anatomy of a right arm, in accordance with some embodiments described herein.

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION OF THE INVENTION

Reference will now be made in detail to the present preferred embodiment(s), examples of which is/are illustrated in the accompanying drawings. Whenever possible, the same reference numerals will be used throughout the drawings to refer to the same or like parts.

FIG. 1 shows some of the anatomy or bodily structure of an arm 10 including a biceps brachii 20, two headed muscle of the arm, which is divided into two tendons proximally. A tendon of the short head 12 of the biceps brachii 20 inserts at the coracoid process 22 on the medial side and is rarely a source of pain. The coracoid process 22 is a short projection from the shoulder blade. The tendon of the short head 12 helps with arm 10 flexion. A tendon of the long head of the biceps 16 of the of the bicep brachii 20 passes over the top of the humerus 18 and inserts at the glenoid cavity 17 (see also, FIG. 2) and is a common source of anterior shoulder pain. The tendon of the long head of the biceps 16 travels deep into the shoulder joint and attaches to the superior aspect of the glenoid labrum. The tendon of the long head of the biceps 16 sits in a deep groove in the humerus 18 called a bicipital groove 18a and the tendon of the long head of the biceps 16 is held in place by a ligament called a transverse humeral ligament. The tendon of the long head of the biceps 16 mainly assists in glenohumeral stability and contributes to arm forward flexion, abduction, and adduction. Rupture of the tendon of the long head of the biceps 16 frequency occurs at the proximal end of the tendon of the long head of the biceps 16 of the bicep brachii 20 at the glenoid cavity 17. It is usually seen in older patients with the average age being in the mid-forties. Other types of biceps brachii 20 ruptures are very rare. Risk factors include age, a history of rotator cuff injuries, recurrent tendinitis, a contralateral biceps tendon rupture, rheumatoid arthritis, and poor conditioning. While a biceps tendon rupture can occur due to overuse or trauma it can also occur after routine activities. Also shown in FIG. 1 is a radius 24, the thicker and shorter of the two bones in the forearm, an insertion of biceps brachii 26, and origins of the biceps brachii 28.

Figure 2:
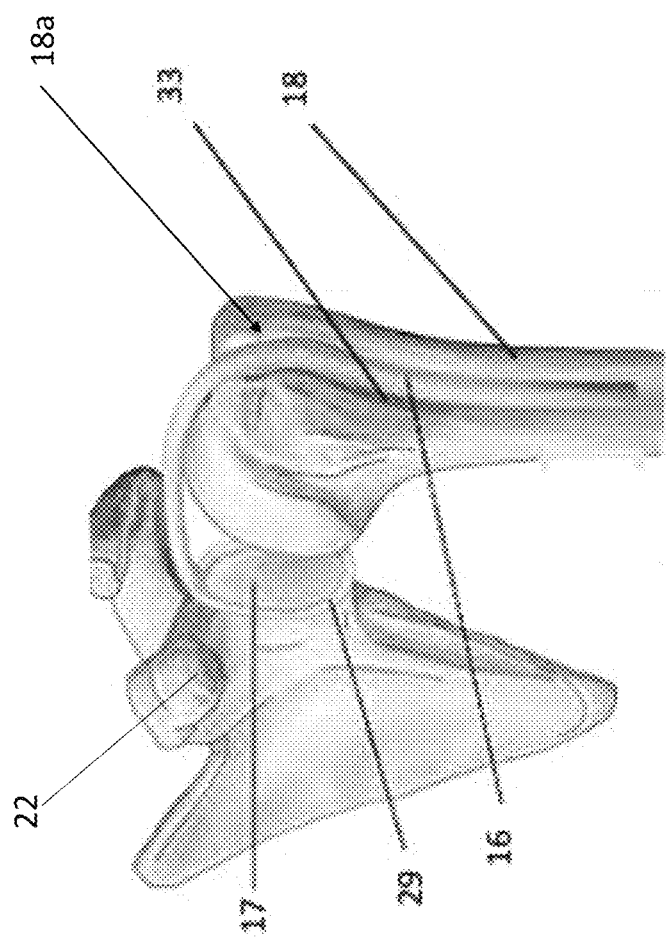
FIG. 2 is a more detailed front left perspective view of a shoulder region of an arm, in accordance with some embodiments described herein.

FIG. 2 is a more detailed front left perspective view of a shoulder region of an arm. While FIG. 2 shows that the tendon of the long head of the biceps 16 travels through the shoulder this is functionally unimportant. Therefore, the tendon of the longhead of the biceps 16 can be secured within the bicipital groove 18a of the humerus 18, the bone of the upper arm, by the proposed arthroscopic staple 300. In various embodiments, an upper portion of the tendon of the long head of the biceps 16 is cut and removed. The bicipital groove 18a allows the tendon of the long head of the biceps 16 to pass through and along the humerus 18. Also shown in FIG. 2 is a tendon of the short head 12 which inserts into the coracoid process 22 outside of the shoulder joint, and labrum 29. This is functional important but is rarely a problem.

Figure 3A:
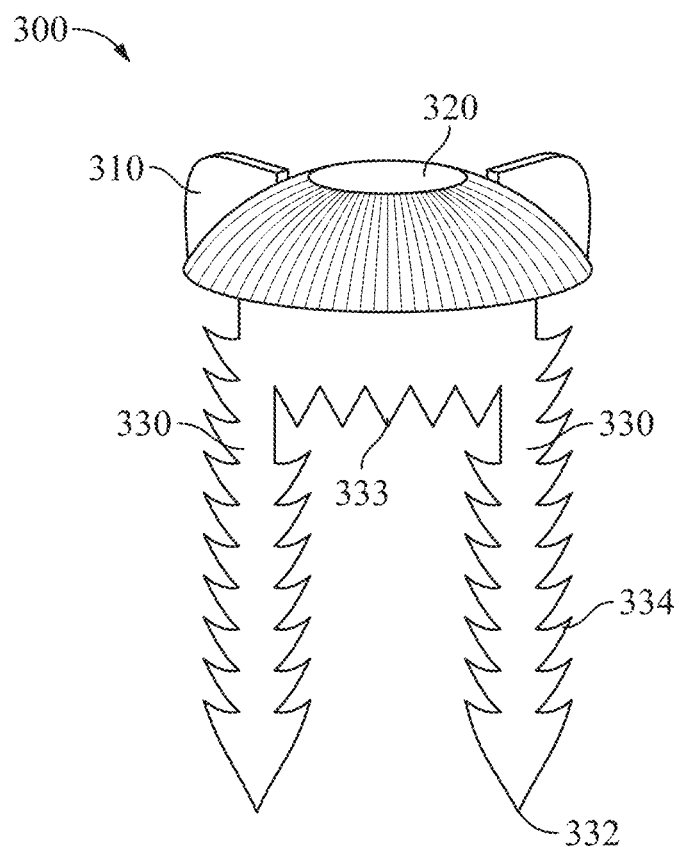
FIG. 3A is a perspective view of an arthroscopic staple, in accordance with some embodiments described herein.

FIG. 3A shows a perspective view of an arthroscopic staple 300 used by a surgeon to arthroscopically fixate the tendon of the long head of the biceps 16 of the biceps brachii 20 in-situ to the humerus 18 within the bicipital groove 18a when performing an arthroscopic high supra-pectoral biceps tenodesis. In various embodiments, the arthroscopic staple 300 is used in an arthroscopic surgical procedure. Arthroscopic surgery, also known simply as arthroscopy, is a minimally invasive orthopedic procedure for diagnosing and treating joint problems. It involves the use of a narrow tube attached to a fiber-optic video camera, an arthroscope, inserted through a tiny keyhole incision. The view inside the joint is transmitted to a high-definition video monitor. In some embodiments, specialized surgical tools access the joint through one or more tiny keyhole incisions. The arthroscopic staple 300 is configured to achieve a reliable and secure bicep tenodesis in the suprapectoral region in a simple arthroscopic procedure.

In various embodiments, the arthroscopic staple 300 comprises a cylindrical body 310. The top of the cylindrical body 310 includes a center aperture 320 formed by a central vertical cavity located at the center of the cylindrical body 310. The cylindrical body 310 includes a first aperture 320a and a second aperture 320b formed by a first vertical cavity and a second vertical cavity radially displaced from the center of the cylindrical body 310.

In various embodiments, the configuration of the arthroscopic staple 300 allows for a primary fixation point. For example, the cylindrical body 310 of the arthroscopic staple 300 comprises a pair of protrusions 330. The pair of protrusions 330 are located on the underside of the cylindrical body 310. Each of the protrusions 330 includes a sharp point 332 and at least one barb 334. A barb is a sharp projection near the end of a sharp point of a protrusion that is angled away from the sharp point to make extraction of the protrusion difficult.

In various embodiments, a diameter of the arthroscopic staple 300 cylindrical body 310 is between about 5 mm and about 10 mm. For example, the diameter of the arthroscopic staple 300 cylindrical body 310 is about 6 mm, about 7 mm, or about 8 mm. The diameter of the arthroscopic staple 300 cylindrical body 310 is between 5 mm and 10 mm. For example, the diameter of the arthroscopic staple 300 cylindrical body 310 is one of about 6 mm, about 7 mm, and about 8 mm. A length of the arthroscopic staple 300 is between about 15 mm and about 25 mm. For example, the length of the arthroscopic staple 300 is about 20 mm. A height of the cylindrical body 310 is between about 3 mm and about 7 mm. For example, the height of the cylindrical body 310 is about 5 mm. In some embodiments, the cylindrical body 310 is a low-profile body with contoured corners.

In some embodiments, the cylindrical body 310 of the arthroscopic staple 300 comprises more than a pair of protrusions 330. For example, the cylindrical body 310 of the arthroscopic staple 300 comprises two pairs of protrusions 330 or four protrusions in total. Each protrusion having a sharp point 332 and at least one barb 334 to make extraction more difficult.

In some embodiments, the tendon of the long head of the biceps 16 is secured with a second arthroscopic staple 300a. For example, the tendon of the long head of the biceps 16 could be secured with a second arthroscopic staple 300a if the tissue of the tendon of the long head of the biceps 16 was of poor quality, or the humerus 18 was too soft, or if the initial arthroscopic staple 300 fixation was deemed to be suspect by the surgeon. In various embodiments, the second arthroscopic staple 300a is secured to the humerus 18 bone superior to the first arthroscopic staple 300 by repeating the steps of the fixation procedure described herein. In some embodiments, the second arthroscopic staple 300a is secured to the humerus 18 inferior to the first arthroscopic staple 300 by repeating the steps of the fixation procedure.

In various embodiments, the arthroscopic staple 300 is made of a polyether ether ketone (PEEK) material. PEEK is a colorless organic thermoplastic polymer belonging to the polyaryletherketone (PAEK) family. PEEK's robustness makes it suitable for demanding applications and PEEK is extensively used in the aerospace, automotive, chemical industries, and the like. Synthesis of PEEK composites has further improved the mechanical and physicochemical properties of PEEK making PEEK well suited for bio-medical applications, including those in the surgical field where PEEK has already been used in spine surgery, orthopedic surgery, maxilla-facial surgery, and the like. Synthesis of PEEK composites has further improved the osteon-inductive and antimicrobial properties through changes in the structure and surface composition of PEEK composites. Osteon-induction is the process by which osteogenesis is induced, the recruitment of immature cells and the stimulation of these cells to develop into pre-osteoblast, a phenomenon that is important for bone formation. Antimicrobial properties of PEEK are important for inhibiting or destroying the growth of microorganism and especially pathogenic microorganisms. For at least these reasons, PEEK based materials are an important biomaterial for bone and cartilage replacement and repair and is therefore the most common, strongest non-metal, and non-absorbent implant material used in sports medicine orthopedic procedures at this time.

In various embodiments, the surface of the arthroscopic staple 300 is smooth. In some embodiments, the surface of the arthroscopic staple 300 is configured to be porous, such that the surface forms a scaffold for the humerus 18 and/or tendon of the long head of the biceps 16. In order not to compromise the strength of the arthroscopic staple 300 only the surface, and not the body of the arthroscopic staple 300 would be configured to be porous.

Figure 3B:
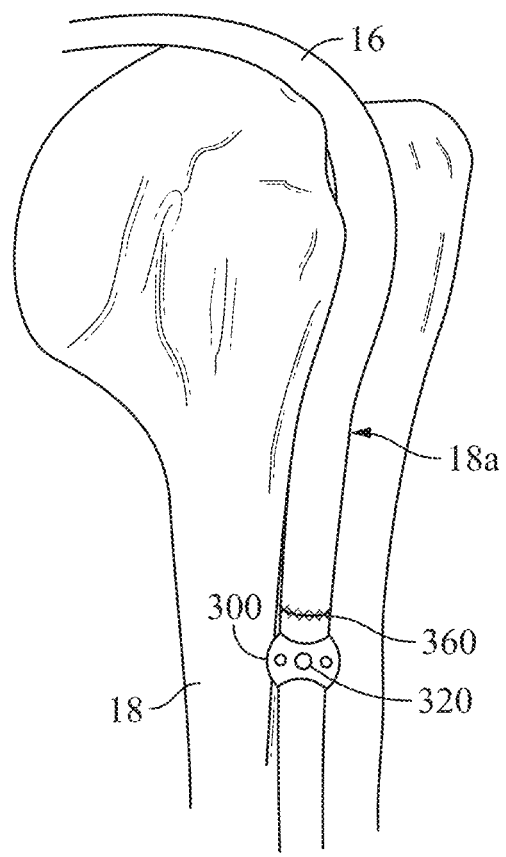
FIG. 3B is a top view of the arthroscopic staple of FIG. 3A coupled to a tendon of the long head of the biceps within a bicipital groove in accordance with some embodiments described herein.

FIG. 3B shows a top view of an arthroscopic staple 300 of FIG. 3A coupled to the tendon of the long head of the biceps 16 of the biceps brachii 20 within the bicipital groove 18a.

In various embodiments, the surgical procedure comprises making a first or standard posterior viewing portal incision and inserting an arthroscope camera. The arthroscopy camera allows the surgeon to see inside the shoulder joint without the need for a large incision and determine the level of the tendon of the long head of the biceps 16 fixation. In some embodiments, the surgeon can repair some types of joint damage with very thin surgical instruments inserted through a small additional incision(s). The arthroscope camera further allows the surgeon to visualize the positioning and insertion of the arthroscopic staple 300 when viewing from the posterior accessory viewing portal.

In various embodiments, the surgical procedure further comprises making a second accessory portal incision, where the second incision is used to introduce a cannula (not shown). In some embodiments, the accessory portal incision is located directly over the bicipital groove 18a. In various embodiments, the surgeon relies entirely on the posterior viewing portal to view the procedure. In some embodiments, the surgeon may also use the accessory portal incision to view at least a portion of the procedure.

The arthroscopic staple 300 is configured to be inserted into the near end of the cannula and slide down an interior of the cannula to the distal end of the cannular tube until the underside of the arthroscopic staple 300 touches a top of the tendon of the long head of the biceps 16 with the aid of a metal tap inserter 500. In various embodiments, a diameter of the cannula is between about 6 mm and about 10 mm. In some embodiments, the diameter of the cannula is between about 7 mm and about 8.5 mm. The body of the cannula is made from a transparent plastic material.

Another advantage of the proposed arthroscopic staple 300 proposed arthroscopic staple 300 is that because the arthroscopic staple 300 is secured while the tendon of the long head of the biceps 16 is still in-situ the arthroscopic staple 300 automatically sets the right tension. There is no need to use subacromial approach, dissect, or move the tendon of the long head. Further, there is no need to prepare either the tendon of the long head of the biceps 16 or the bicipital groove 18a. However, if the tendon of the long head of the biceps 16 is torn or detached then the tendon of the long head of the biceps 16 will need to be set to the right tension prior to the insertion of the arthroscopic staple 300.

Figure 3C:
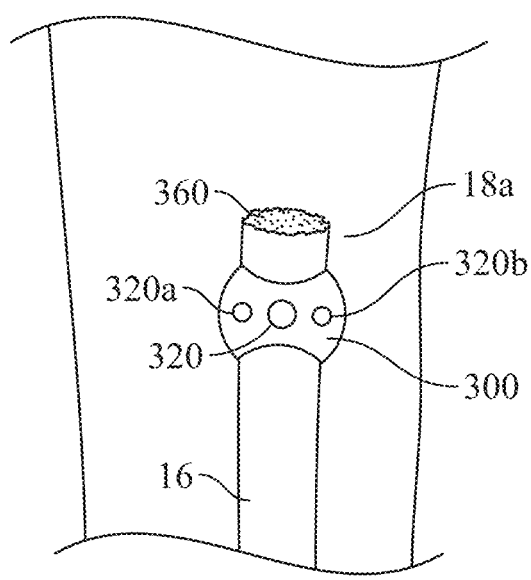
FIG. 3C is a more detailed top view of the arthroscopic staple of FIG. 3B with a portion of the tendon of the long head removed, in accordance with some embodiments described herein.

FIG. 3C shows a more detailed top view of an arthroscopic staple 300 of FIG. 3A coupled to the tendon of the long head of the biceps 16 of the biceps brachii 20 within the bicipital groove 18a. In FIG. 3C a portion of the tendon of the long head of the biceps 16 of the biceps brachii 20 has been removed.

Another advantage of the proposed arthroscopic staple 300 is that there is no need to deliver the tendon of the long head of the biceps 16 to the open air with either fixation method. That is, the arthroscopic staple 300 is used to arthroscopically fixate the tendon of the long head of the biceps 16 in-situ to the humerus 18 in the bicipital groove 18a when performing an arthroscopic high supra-pectoral biceps tenodesis. After the arthroscopic staple 300 has been tapped and/or pressed into place the tendon of the long head of the biceps 16 is then amputated 360 proximal to the arthroscopic staple 300 using arthroscopic scissors or cautery device. The remaining stump of the tendon of the long head of the biceps 16 and any dead tissue or extraneous material is removed. In various embodiments, the amputated stump of the tendon of the long head of the biceps 16 and any dead tissue or extraneous material is removed through the cannula. In some embodiments, the portion of the tendon of the long head of the biceps 16 to be amputated is shaved in-situ and removed using a shaver suction device.

While the arthroscopic staple 300 is used to fixate the tendon of the long head of the biceps 16 in-situ to the humerus 18 in the biceps grove the arthroscopic staple 300 can also be used to fixate a torn long head tendon of the long head of the biceps 16 or detached tendon of the long head of the biceps 16 into the humerus 18 in the bicep grove.

Figure 4:
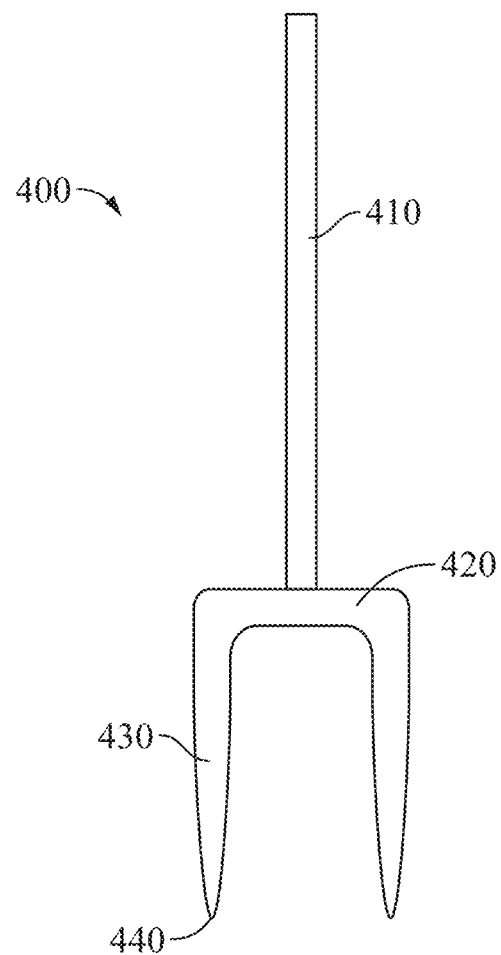
FIG. 4 is side view of a metal tap pitchfork, in accordance with some embodiments described herein.

FIG. 4 shows a side view of a metal tap pitchfork 400 that is used by a surgeon when performing an arthroscopic high supra-pectoral biceps tenodesis with the arthroscopic staple 300 of FIG. 3A.

Another advantage of the proposed arthroscopic staple 300 is that the configuration of the arthroscopic staple 300 does not require moving the tendon of the long head of the biceps 16 from its resting location to create pilot holes 610.

In various embodiments, a metal tap pitchfork 400 is used to make a pair of pilot holes 610 in the humerus 18 for the arthroscopic staple 300. The metal tap pitchfork 400 comprises a rod 410 attached to the top of a body 420 with a pair of protrusions 430 attached to the underside of the body 420. Each protrusion 430 has a length of about 15 mm and tapers and to a sharp point. The spacing between the two protrusions 430 is configured to match the width of the barbed prongs 330 of the arthroscopic staple 300. The spacing will therefore be dependent on the size of the arthroscopic staple 300 selected for the procedure.

In various embodiments, a cannula is placed into the accessory porta incision and the metal pitchfork tap 400 is placed over the tendon of the long head of the biceps 16 and tapped to form the arthroscopic staple pilot holes 610. In various embodiments, the metal tap pitchfork 400 is tapped until a base of the metal tap pitchfork 400 bottoms out on the tendon of the long head of the biceps 16, whereupon the metal tap pitchfork 400 is removed from the cannula.

In various embodiments, the size of the arthroscopic staple 300 is substantially the same for all of the most common recipients of this procedure, namely people of high school age and older. It is very uncommon for this procedure to be performed on people who are not within this age group.

In some embodiments, there will be a dedicated metal tap pitchfork 400 for each arthroscopic staple 300 size. The length of the rod 410 of the metal pitchfork tap 400 is between about 15 cm and about 25 cm. For example, in some embodiments, the length of the rod 410 is about 22 cm.

In some embodiments, the cylindrical body 310 of the arthroscopic staple 300 comprises more than a pair of protrusions 330. For example, the cylindrical body 310 of the arthroscopic staple 300 comprises two pairs of protrusions 330 or four protrusions in total and the metal tap pitchfork 400 has a corresponding number of protrusions 430 or sharp points 440 with the same spacing as the protrusions 330 on the arthroscopic staple 300.

Figure 5:
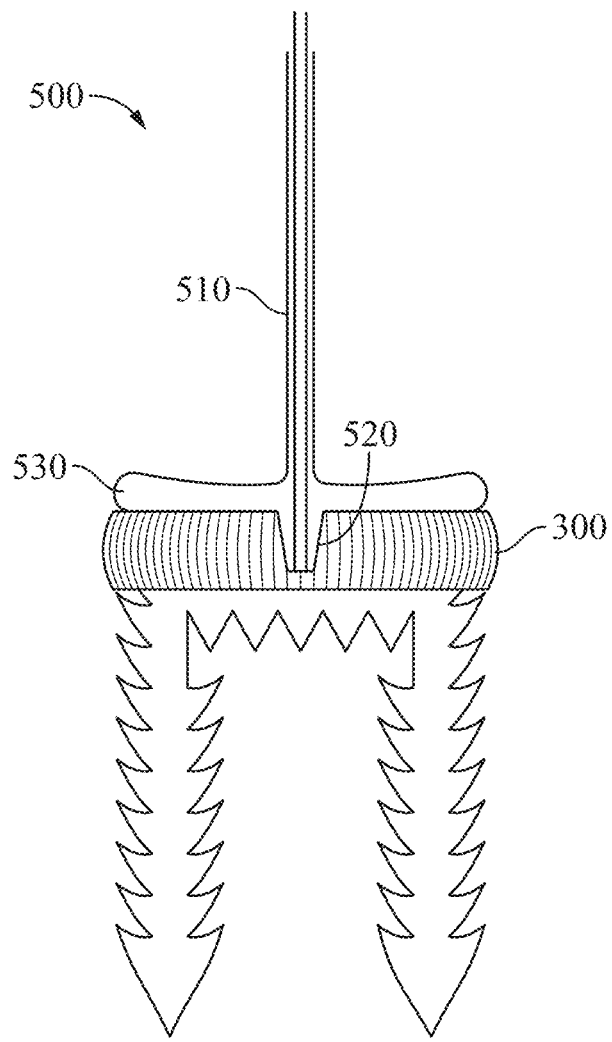
FIG. 5 is a side view of a metal tap inserter coupled to the arthroscopic staple of FIG. 3A, in accordance with some embodiments described herein.

FIG. 5 shows a side view of a metal tap inserter 500 coupled to the arthroscopic staple 300 of FIG. 3A that is used by a surgeon when performing an arthroscopic high suprapectoral biceps tenodesis.

In various embodiments, the metal tap inserter 500 is used to position and align the pair of protrusions 330 of the arthroscopic staple 300 so that the arthroscopic staple 300 straddles the tendon of the long head of the biceps 16 and there is a single protrusion 330 on each side of the tendon of the long head of the biceps 16. In various embodiment, a metal tap inserter 500 is used to tap the arthroscopic staple 300 into the humerus 18. The metal tap inserter 500 is configured to be inserted into the near end of the cannula (not shown) and slid down the cannula.

In various embodiments, the metal tap inserter 500 is tapped until a base of the arthroscopic staple 300 bottoms out on the tendon of the long head of the biceps 16, whereupon the metal tap inserter 500 is detached from the arthroscopic staple 300 and removed from the cannula.

Another advantage of the proposed arthroscopic staple 300 is that the arthroscopic staple 300 does not impale, split, or damage the healthy portion of the tendon of the long head of the biceps 16. In some embodiments, the bottom of the body of the arthroscopic staple 300 is contoured to substantially match the shape of the tendon of the long head of the biceps 16. The bottom surface of the arthroscopic staple 300 may have a rough or uneven surface configured to lockingly engage the tendon of the long head of the biceps 16 and prevent the tendon of the long head of the biceps 16 from slipping. For example, the bottom surface of the arthroscopic staple 310 comprises a plurality of protrusions 333. In some embodiments, the bottom surface of the arthroscopic staple 300 may be coated with a material that increases the friction between the bottom of the body of the arthroscopic staple 300 and the tendon of the long head of the biceps 16.

In various embodiments, the metal tap inserter 500 is used to align the pair of protrusions 330 of the arthroscopic staple 300 with the pilot holes 610 made in the humerus 18 by the metal tap pitchfork 400. In various embodiments, the metal tap inserter 500 is used to tap and/or press the arthroscopic staple 300 into the pilot holes 610 made by the metal tap pitchfork 400.

In various embodiments, the inserter 500 is a long rod made of a metal material. In various embodiments, the material used for the metal tap inserter 500 includes stainless steel, cobalt-chromium alloys, titanium alloys, and the like. In various embodiments, metal tap inserter 500 is reusable and made of a durable, machine washable material that can be disinfected and sterilized. In some embodiments, the metal tap inserter 500 is a disposable solution, and the metal tap inserter 500 is recycled or safely disposed of to prevent infections and cross contamination between different patients.

In various embodiments, the metal tap inserter 500 is coupled to the top of the arthroscopic staple 300. For example, the distal end of the metal tap inserter 500 may be configured to be pressed into and lockingly engage the top of the arthroscopic staple 300 by means of a substantially matching recess. One or more of the distal ends of the metal tap inserter 500 and the recess in the top of the body of arthroscopic staple 300 may be tapered.

In another embodiment, the distal end 520 of the metal tap inserter 500 may be threaded and be configured to lockingly engage the top of the body of arthroscopic staple 300 by means of a matching threaded recess. The length of a rod 510 of the metal tap inserter 500 is between about 15 cm and about 25 cm. For example, in some embodiments, the length of the rod 510 is about 22 cm.

In various embodiments, the diameter of the metal tap inserter 500 is significantly smaller than the diameter of the arthroscopic staple 300 so that the center aperture 320 in the arthroscopic staple 300 does not unduly weaken the structural integrity of the arthroscopic staple 300. For example, the diameter of the metal tap inserter 500 is equal to or less than about 3 mm. In some embodiments, the portion of the metal tap inserter 500 configured to engage the top of the arthroscopic staple 300 is stepped and the body of the metal tap inserter 500 is equal to or greater than about 3 mm. For example, the diameter of the shoulder and/or rod 510 of the metal tap inserter 500 is about the same as the diameter of the arthroscopic staple 300 while the portion of the metal tap inserter 500 configured to engage the arthroscopic staple 300 is significantly smaller so not to weaken the structural integrity of the arthroscopic staple 300.

In various embodiments, the material used for the metal tap inserter 500 includes stainless steel, cobalt-chromium alloys, titanium alloys, and the like. In various embodiments, the metal tap inserter 500 is reusable and made of a durable, machine washable material that can be disinfected and sterilized. In some embodiments, the metal tap inserter 500 is disposable solution, and the metal tap inserter 500 is recycled or safely disposed of to prevent infections and cross contamination between different patients.

Another advantage of the proposed arthroscopic staple 300 is that the configuration of the arthroscopic staple 300 allows for rapid additional suture 326 back-up fixation. In some embodiments, the configuration of the arthroscopic staple 300 allows for a secondary fixation method in addition to the primary fixation method. For example, the cylindrical body 310 of the arthroscopic staple 300 comprises one or more apertures 320*a* and 320*b* formed by a vertical cavity in the cylindrical body 310 of the arthroscopic staple 300. The vertical cavity(s) allow at least one suture 326 looped around the tendon of the long head of the biceps 16 and/or through the tendon of the long head of the biceps 16 to be fed through the vertical cavities to the top of the cylindrical body 310 of the arthroscopic staple 300 prior to tapping the arthroscopic staple 300 into place. The suture 326 is then tied over the top of the arthroscopic staple 300 as a back-up fixation point.

Figure 6A:
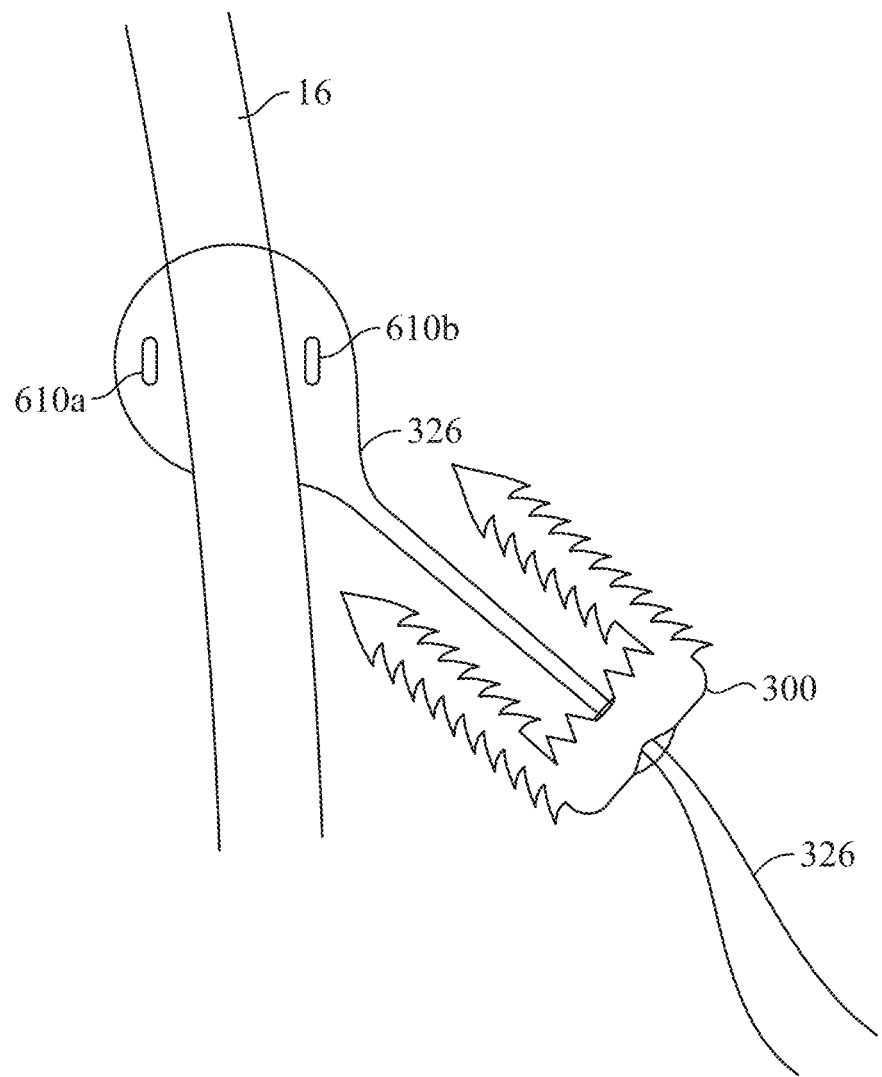
FIG. 6A is a perspective view of the arthroscopic staple of FIG. 3A and a suture looped around the tendon of the long head, in accordance with some embodiments described herein.

FIG. 6A shows a perspective view of the arthroscopic staple 300 of FIG. 3A and a suture 326 looped around the tendon of the long head of the biceps 16 of the biceps brachii 20 within the bicipital groove (see FIGS. 1-2).

In various embodiments, the suture 326 comprises a first end 326*a* and a second end 326*b*. The first end of the suture 326 is looped around the tendon of the long head of the biceps 16 and/or through the tendon of the long head of the biceps 16 and fed through the first aperture 320*a* in the cylindrical body 310 of the arthroscopic staple 300. The first end of the suture 326 is then fed through the second aperture 320*b* in the cylindrical body 310 of the arthroscopic staple 300. The first end 326*a* and the second end 326*b* of the suture 326 are tied over the top of the arthroscopic staple 300 to further secure the arthroscopic staple 300 in place.

Figure 6B:
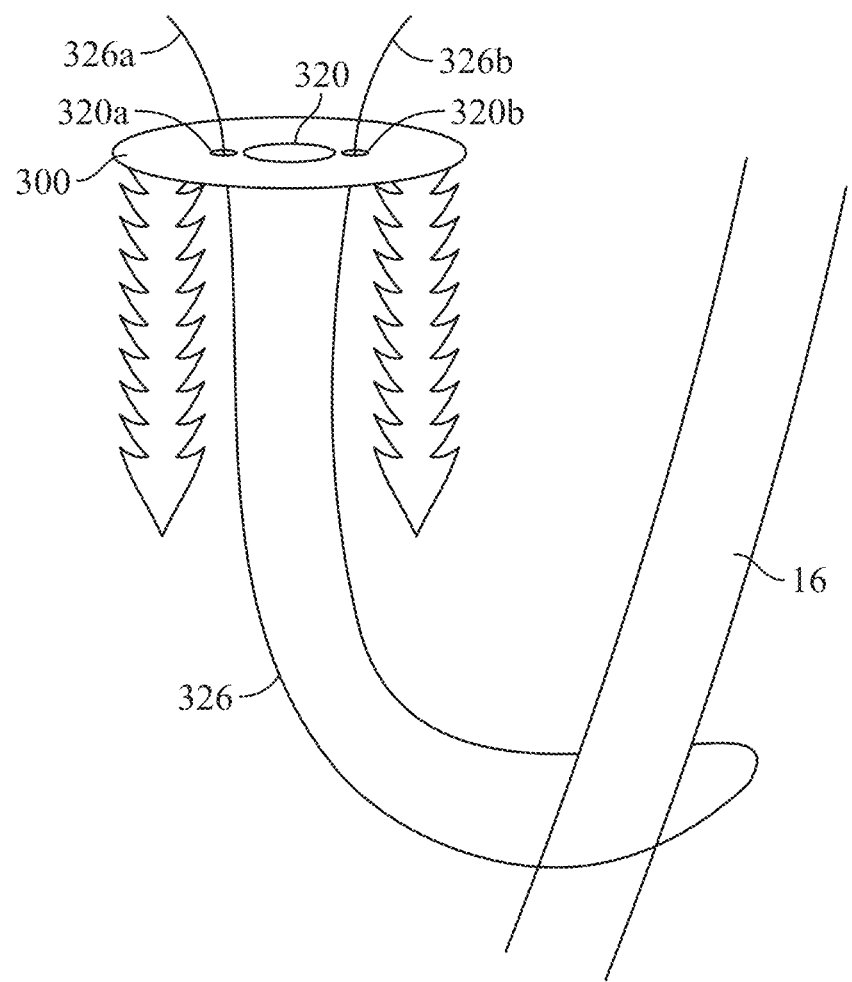
FIG. 6B is a more detailed perspective view of the arthroscopic staple of FIG. 3A, with a suture looped around the tendon of the long head and threated through apertures in the arthroscopic staple, in accordance with some embodiments described herein.

FIG. 6B shows a more detailed perspective view of the arthroscopic staple 300 of FIG. 3A, with a suture 326 looped around the tendon of the long head of the biceps 16 and threaded through apertures 320*a* and 320*b* in the arthroscopic staple 300 before being tied off.

While the arthroscopic staple 300, metal tap pitchfork 400, and metal tap inserter 500 are described in the context of securing tendon of the long head of the biceps 16 other types of tendons are contemplated as well.

While preferred embodiments of the present invention have been shown and described herein, it will be obvious to those skilled in the art that such embodiments are provided by way of example only. Numerous variations, changes, and substitutions will now occur to those skilled in the art without departing from the invention, in accordance with the claims. It should be understood that various alternatives to the embodiments of the invention described herein may be employed in practicing the invention.

What is claimed is:

1. An arthroscopic staple, the arthroscopic staple comprising:
   a cylindrical body comprising a polyether ether ketone (PEEK) material; and
   wherein a top of the cylindrical body comprises a center aperture formed by a central vertical cavity located at a center of the cylindrical body, and
   wherein the cylindrical body comprises a first aperture and a second aperture formed by a first vertical cavity and a second vertical cavity radially displaced from the center of the cylindrical body, wherein the first aperture and the second aperture of the cylindrical body are operable to allow at least one suture looped around a biceps tendon to be fed through the cylindrical body and tied off;
   a first pair of protrusions located on an underside of the cylindrical body, wherein each of the first pair of protrusions comprises a sharp point and at least one barb, wherein the sharp point is constructed and arranged to make one or more pilot holes in a bone for an arthroscopic staple.

2. The arthroscopic staple of claim 1, wherein each of the at least one barb is a sharp projection located near and angled away from an end of the sharp point of each of the first pair of protrusions to make extraction of the arthroscopic staple difficult from a bone.

3. The arthroscopic staple of claim 1, wherein a diameter of the cylindrical body is between 5 mm and 10 mm and wherein a height of the cylindrical body is between 3 mm and 7 mm.

4. The arthroscopic staple of claim 1, wherein the cylindrical body has a low-profile body with rounded corners.

5. The arthroscopic staple of claim 1, wherein the cylindrical body of the arthroscopic staple has a height of 5 mm.

6. The arthroscopic staple of claim 1, wherein a length of each of the first pair of protrusions of the cylindrical body is between 10 mm and 20 mm.

7. The arthroscopic staple of claim 1, wherein a portion of the underside of the cylindrical body between the first pair of protrusions is contoured to lockingly engage a biceps tendon ranging from about 6 mm wide to about 3 mm thick, and wherein at least the portion of the underside of the cylindrical body is coated with a material having a high coefficient of static friction.

8. The arthroscopic staple of claim 1, wherein the center aperture of the cylindrical body is operable to lockingly engage a distal end of an inserter rod, wherein the inserter rod is operable to tap the first pair of protrusions of the cylindrical body into a bone, and wherein the distal end of the inserter rod is threaded to engage a matching threaded recess in the center aperture of the cylindrical body.

9. The arthroscopic staple of claim 1, wherein the center aperture of the cylindrical body and a distal end of a metal tap inserter are operable to form an interference fit, wherein the metal tap inserter is operable to tap the first pair of protrusions of the cylindrical body into a bone, and wherein an internal diameter of the center aperture of the cylindrical body is between 1 mm and 3 mm.

10. The arthroscopic staple of claim 1, further comprising a second pair of protrusions located on the underside of the cylindrical body, wherein each of the second pair of protrusions comprises a sharp point and at least one barb, and wherein each of the at least one barb is a sharp projection located near and angled away form an end of the sharp point of each of the second pair of protrusions to make extraction of the arthroscopic staple difficult from a bone.

11. A metal tap inserter for an arthroscopic staple, the metal tap inserter comprising:
   a solid cylindrical rod comprising a body between 6.5 mm and 8 mm in diameter, wherein the solid cylindrical rod is made of a material that is metal, and wherein a distal end of the solid cylindrical rod is operable to be lockingly coupled to a recess in the arthroscopic staple and a near end of the solid cylindrical rod is operable to be gently and repeatedly struck with a surgical mallet.

12. The metal tap inserter of claim 11, wherein a length of the solid cylindrical rod is between 15 cm and 25 cm and wherein a diameter of the solid cylindrical rod is between 1 mm and 3 mm.

13. The metal tap inserter of claim 11, wherein a tip portion of the distal end of the solid cylindrical rod is between 1 mm and 3 mm in diameter, and wherein the tip portion of the distal end of the solid cylindrical rod has a shoulder.

14. The metal tap inserter of claim 11, wherein the distal end of the solid cylindrical rod has a thread that lockingly couples with a thread in the recess in the arthroscopic staple, and wherein a tip of the distal end of the solid cylindrical rod has a taper and no thread.

15. The metal tap inserter of claim 11, wherein the solid cylindrical rod is made of a material that is one or more of a surgical grade stainless steel, a cobalt-chromium alloy, and a titanium alloy.

16. A metal tap pitchfork for an arthroscopic staple, the metal tap pitchfork comprising:

a pitchfork body;
a solid cylindrical rod coupled to an upper face of the pitchfork body; and
a pair of protrusions coupled to an underside of the pitchfork body for use with a two-pronged staple or two pairs or protrusions coupled to an underside of the pitchfork body for use with a four-pronged staple, wherein each of the pair of protrusions located on an underside of the pitchfork body has a length of 15 mm and tapers to a sharp point operable to make a pilot hole for the arthroscopic staple.

17. The metal tap pitchfork of claim 16, wherein the metal tap pitchfork is made of a material that is one or more of a surgical grade stainless steel, a cobalt-chromium alloy, and a titanium alloy.

18. The metal tap pitchfork of claim 16, wherein the length of the solid cylindrical rod is between 15 cm and 25 cm, and wherein a distance between the pair of protrusions is 6 mm.

* * * * *